(12) United States Patent
    Zhou

(10) Patent No.: US 9,592,339 B2
(45) Date of Patent: Mar. 14, 2017

(54) SYRINGE PUMP AND DRIVE SYSTEM THEREOF

(71) Applicant: Zensun (Shanghai) Science & Technology Limited, Shanghai (CN)

(72) Inventor: Mingdong Zhou, Shanghai (CN)

(73) Assignee: Zensun (Shanghai) Science & Technology Limited, Shanghai (CN)

( * ) Notice: Subject to any disclaimer, the term of this patent is extended or adjusted under 35 U.S.C. 154(b) by 491 days.

(21) Appl. No.: 14/359,080

(22) PCT Filed: Nov. 21, 2012

(86) PCT No.: PCT/CN2012/084936
§ 371 (c)(1),
(2) Date: May 16, 2014

(87) PCT Pub. No.: WO2013/075622
PCT Pub. Date: May 30, 2013

(65) Prior Publication Data
US 2014/0323971 A1    Oct. 30, 2014

(30) Foreign Application Priority Data
Nov. 21, 2011    (CN) .......................... 2011 1 0411448

(51) Int. Cl.
*A61M 5/168*    (2006.01)
*A61M 5/142*    (2006.01)

(52) U.S. Cl.
CPC .... *A61M 5/16886* (2013.01); *A61M 5/14216* (2013.01); *A61M 5/1684* (2013.01); *A61M 2205/3389* (2013.01)

(58) Field of Classification Search
CPC ............ A61M 5/14216; A61M 5/1452; A61M 5/168; A61M 5/1684; A61M 5/16886;
(Continued)

(56) References Cited

U.S. PATENT DOCUMENTS 5,295,967 A     3/1994  Rondelet et al.
5,569,212 A *  10/1996  Brown ................ A61M 5/1782
                                                  128/DIG. 1
(Continued)

FOREIGN PATENT DOCUMENTS

CN       87211127       10/1988
CN       101138659 A     3/2008

OTHER PUBLICATIONS

International Search Report dated Feb. 28, 2013, for International Application No. PCT/CN2012/084936, filed Nov. 11, 2012.

*Primary Examiner* — Kami A Bosworth
(74) *Attorney, Agent, or Firm* — Jones Day

(57) ABSTRACT

Disclosed is a drive system of a syringe pump, comprising: an outer sleeve (11) having an inner wall provided with a resistive sheet slot and a conductive sheet slot, both of which slot extending axially; a resistive sheet (12) provided in the resistive sheet slot and a conductive sheet (13) provided in the conductive sheet slot; an injection pushrod (14) slidably provided in the outer sleeve (11), wherein a hermetic seal is maintained between the injection pushrod (14) and the inner wall of the outer sleeve (11), and a cavity having an opening is provided on the injection pushrod (14), with the opening of the cavity being provided at a tail end of the injection pushrod (14); an elastic conductive contact sheet (15) fixedly provided on the injection pushrod (14), with one end of the elastic conductive contact sheet (15) being in contact with the conductive sheet (13) and the other end being in contact with the resistive sheet (12); and a drive device provided in the cavity and driving the injection pushrod (14) to move forth and back. The drive system can ensure the accuracy of administration.

8 Claims, 2 Drawing Sheets

(58) Field of Classification Search
CPC .... A61M 5/172; A61M 5/178; A61M 5/3129; A61M 5/315; A61M 5/31528; A61M 5/31568; A61M 2005/2086; A61M 2005/3143; A61M 2205/3389
See application file for complete search history.

(56) References Cited

U.S. PATENT DOCUMENTS

| | | | |
|---|---|---|---|
| 6,110,148 A * | 8/2000 | Brown | A61M 5/1782 |
| | | | 222/23 |
| 7,195,616 B2 | 3/2007 | Diller et al. | |
| 7,255,690 B2 | 8/2007 | Gray et al. | |
| 2005/0020980 A1 * | 1/2005 | Inoue | A61M 5/14244 |
| | | | 604/152 |
| 2007/0073236 A1 | 3/2007 | Mernoe et al. | |
| 2007/0123829 A1 | 5/2007 | Atterbury et al. | |

* cited by examiner

SYRINGE PUMP AND DRIVE SYSTEM THEREOF

This application claims the priority to Chinese patent application No. 201110411448.9, filed with the Chinese Patent Office on Nov. 21, 2011, titled "DRIVE SYSTEM OF PORTABLE SYRINGE PUMP", which is incorporated by reference herein in its entirety.

FIELD OF THE INVENTION

The present invention relates to the technical field of medical devices, and in particular to a syringe pump and a drive system thereof.

BACKGROUND OF THE INVENTION

Syringe pumps are infusion assist devices commonly used in the clinic, which are mainly used for the precise infusion of certain particular drugs or high-risk drugs, and can be used to maintain a certain index value of a patient to be constant or used for continuous administration of drugs in order to achieve a better effect of administration. The devices create an advantageous condition for administration to first-aid patients, critically ill patients, particular patients and children, and improve the efficiency of medical personnel. However, it should be paid attention to that such a product will directly influence the administration safety and efficacy for the patients, if an abnormal control of the infusion flow rate occurs.

From 2002 to the end of 2010, National Center for ADR Monitoring, China had received 575 *Reports on Suspicious Adverse Event of Medical Device* relating to infusion pumps and syringe pumps in total, in which 216 reports are related to syringe pumps. These adverse events mainly include: abnormal control of the infusion flow rate, failing to pump medical fluids, system halt, leakage of infusion lines, and so on. Among these, there are 216 reports that show an abnormal infusion flow rate, in which 61 reports are related to syringe pumps (accounting for 28% of the total reports about syringe pumps).

A too fast infusion rate may cause an overdose and thus a toxicity occurrence, while a too slow infusion rate may cause an excessively small drug dose which is short of the therapeutic effect. Inaccurate control of the syringe pump rate may be associated with the software and the type, performance, etc. of related consumables (infusion lines and syringes) used. Another very important reason may be that the monitor system designed for the syringe pump is inadequate, such that the accuracy of the infusion flow rate cannot be ensured. A commercially available syringe pump generally has an electronic device for detecting the operating condition of a motor at a trailing end of the motor. However, as operation of the motor requires driving running of a injection pushrod by drive threads of a reducer and the reducer output shaft, which undergoes a series of motion conversion, a normal operation of the motor cannot fully ensure either a normal operation of the injection pushrod or the accuracy of administration, and thus there still exist potential safety risks.

SUMMARY OF THE INVENTION

The present invention provides a drive system of a syringe pump, which can ensure the accuracy of administration. The present invention also provides a syringe pump comprising the drive system described above.

The drive system of the syringe pump according to the present invention comprises:

an outer sleeve, with an inner wall provided with a resistive sheet slot and a conductive sheet slot, both of which slot extending axially;

a resistive sheet provided in the resistive sheet slot and a conductive sheet provided in the conductive sheet slot;

an injection pushrod slidably provided in the outer sleeve, wherein a hermetic seal is maintained between the injection pushrod and the inner wall of the outer sleeve, and a cavity having an opening is provided on the injection pushrod, the opening of the cavity being provided at a tail end of the injection pushrod;

an elastic conductive contact sheet fixedly provided on the injection pushrod, one end of the elastic conductive contact sheet being in contact with the conductive sheet and the other end being in contact with the resistive sheet; and a drive device provided in the cavity and driving the injection pushrod to move forth and back.

Preferably, the drive device comprises a motor arranged in the cavity and connected with the outer sleeve, a reducer connected with the motor and a lead screw connected with the reducer; the inner wall of the cavity is provided with inner threads extending axially and mating with the lead screw; and the inner wall of the outer sleeve is provided with a rotation-limiting chute extending axially, the injection pushrod being provided with an anti-rotation pin slidably mating with the rotation-limiting chute.

Preferably, fixed legs are provided on the outer periphery of the motor and annular bulges are provided on the inner wall of the outer sleeve, with inner sides of the fixed legs abutting against the annular bulges; the drive system also comprises an inner cover abutting against outer sides of the fixed legs and an outer cover covering the inner cover and fixedly connected with the outer sleeve, with a pressure sensor being provided between a top of the inner cover and a top of the outer cover.

Preferably, the elastic conductive contact sheet comprises a conductive ferrule portion sleeved onto the outer periphery of the injection pushrod and at least two conductive contact pin portions connected to the conductive ferrule portion, wherein at least one of the conductive contact pin portions contacts the resistive sheet and at least one of the conductive contact pin portions contacts the conductive sheet.

Preferably, the outer periphery of the outer sleeve has a square-shaped cross-section.

Preferably, a sealing ring is provided between a head of the outer sleeve and the injection pushrod.

Preferably, an encoder for detecting an operation of the motor on a trailing end of the motor.

The present invention also provides a syringe pump comprising any of the drive systems as described above.

Compared with a drive system of a syringe pump in the prior art, in the drive system according to the present invention, the inner wall of the outer sleeve is fixedly provided with the resistive sheet and the conductive sheet that extend axially, the injection pushrod is axially slidable along the outer sleeve under the driving of the drive device, and the outer periphery of the injection pushrod is provided with the elastic conductive contact sheet that enables the conductive sheet and the resistive sheet to be in conductive communication with each other, so that as the injection pushrod moves, contact positions between the elastic conductive contact sheet and the conductive sheet and between the elastic conductive contact sheet and the resistive sheet both vary continuously, and in turn, a resistance from the resistive sheet to the conductive sheet varies continuously, and the position of the injection pushrod can be known by measuring the resistance between the resistive sheet and the conductive sheet. Accordingly, the present invention can precisely control the amount of a medical fluid infused by the injection pushrod, by measuring the resistance between the resistive sheet and the conductive sheet.

The present invention also provides a syringe pump comprising the drive system as described above. Similarly, the syringe pump according to the present invention can ensure the accuracy of administration.

BRIEF DESCRIPTION OF DRAWINGS

In FIGS. 1-3:
outer sleeve—11;
resistive sheet—12;
conductive sheet—13;
injection pushrod—14;
elastic conductive contact sheet—15;
motor—16;
reducer—17;
lead screw—18;
inner cover—19;
outer cover—20;
pressure sensor—21.

DETAILED DESCRIPTION OF EMBODIMENTS

An embodiment according to the present invention specifically provides a drive system of a syringe pump, which can ensure the accuracy of administration. This embodiment also provides a syringe pump comprising the drive system described above.

The technical solution in embodiments of the present invention will now be clearly and fully described below with reference to the drawings, and it is clear that the described embodiments are only a part of, not all of embodiments of the present invention. All other embodiments that are made from these embodiments by one of ordinary skill in the art without departing from the spirit and scope of the present invention would fall within the claimed scope of the invention.

Figure 1:
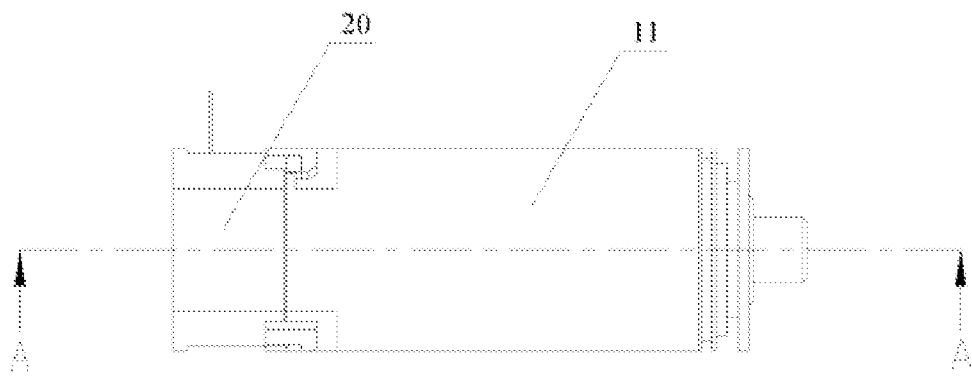
FIG. 1 is a schematic diagram showing an exterior structure of a drive system according to an embodiment of the present invention.
Figure 2:
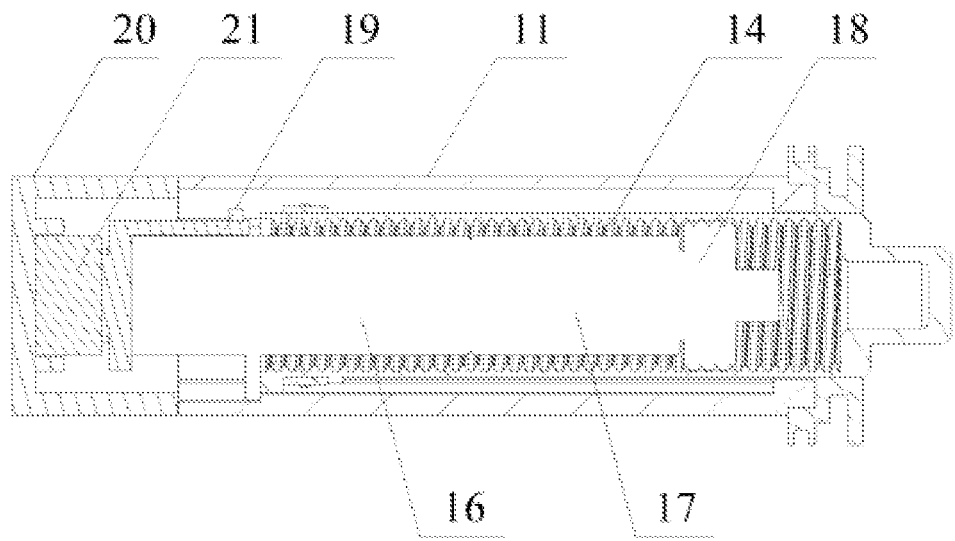
FIG. 2 is a schematic sectional view taken along line A-A in FIG. 1.
Figure 3:
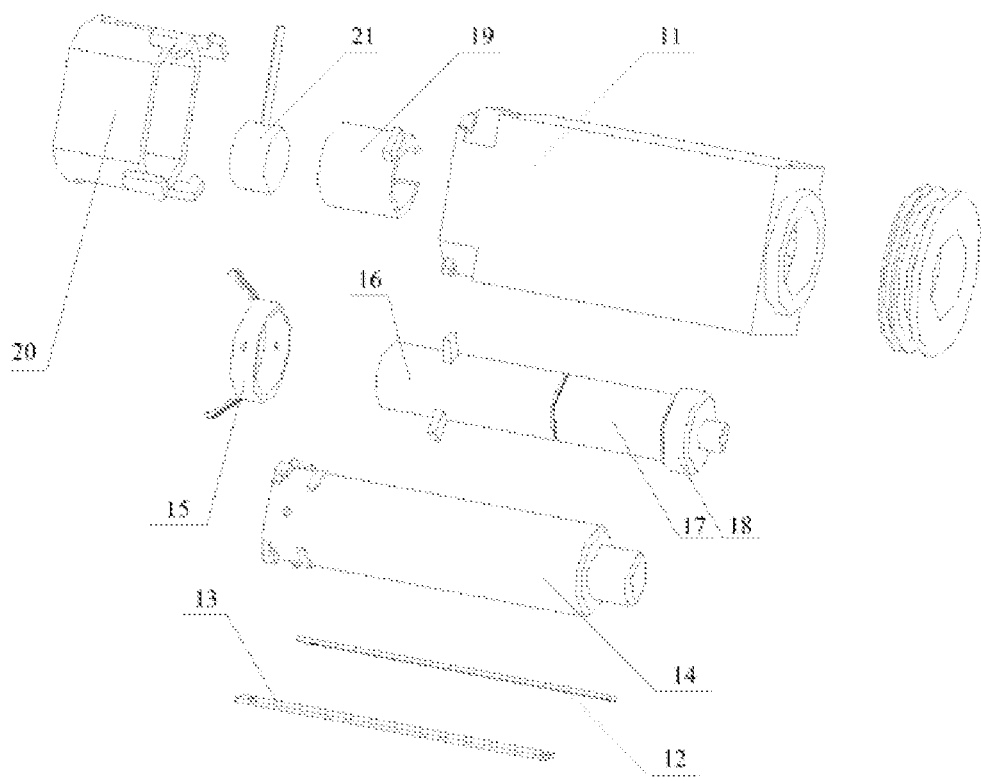
FIG. 3 is a schematic diagram showing an exploded structure of the drive system according to an embodiment of the present invention.

Referring to FIGS. 1-3, the drive system of the syringe pump according to the embodiment comprises an outer sleeve 11 with an inner wall thereof being provided with a resistive sheet slot and a conductive sheet slot, both of which slot extend axially. A resistive sheet 12 is provided in the resistive sheet slot, and a conductive sheet 13 is provided in the conductive sheet slot.

The drive system also comprises an injection pushrod 14 slidably provided in the outer sleeve 11. A hermetic seal is maintained between the injection pushrod 14 and the inner wall of the outer sleeve 11 so as to prevent medical fluid leakage from between the injection pushrod 14 and the inner wall of the outer sleeve 11. A cavity having an opening that is provided at a tail end of the injection pushrod 14 is provided on the injection pushrod 14.

An elastic conductive contact sheet 15 is fixed on the injection pushrod 14. One end of the elastic conductive contact sheet 15 is in contact with the conductive sheet 13 and the other end in contact with the resistive sheet 12, such that a closed loop can be formed by the resistive sheet 12, the elastic conductive contact sheet 15 and the conductive sheet 13.

The drive system also comprises a drive device provided in the cavity and driving the pushrod to move forth and back.

As such, in the drive system according to the embodiment, the inner wall of the outer sleeve 11 is fixedly provided with the resistive sheet 12 and the conductive sheet 13 that extend axially, the injection pushrod 14 is axially slidable along the outer sleeve 11 under the driving of the drive device, and the outer periphery of the injection pushrod 14 is provided with the elastic conductive contact sheet 15 that enables the conductive sheet 13 and the resistive sheet 12 to be in conductive communication with each other, so that as the injection pushrod 14 moves, contact positions between the elastic conductive contact sheet 15 and the conductive sheet 13 and between the elastic conductive contact sheet 15 and the resistive sheet 12 both vary continuously, and in turn, a resistance from the resistive sheet 12 to the conductive sheet 13 varies continuously, and the position of the injection pushrod 14 can be inferred by measuring the resistance between the resistive sheet 12 and the conductive sheet 13. Accordingly, the embodiment can precisely control the amount of a medical fluid infused by the injection pushrod 14, by measuring the resistance between the resistive sheet 12 and the conductive sheet 13.

It should be noted that, the drive device described above may be a drive device that can provide a stable linear driving force, such as a linear motor. For example, the drive device described above may also be configured as follows.

The drive device comprises a motor 16 provided in the cavity and connected with the outer sleeve 11, a reducer 17 connected with the motor 16, and a lead screw 18 connected with the reducer 17.

An inner wall of the cavity of the outer sleeve 11 is provided with inner threads extending axially and mating with the lead screw 18; and the inner wall of the outer sleeve 11 is provided with a rotation-limiting chute extending axially, and the injection pushrod 14 is provided with an anti-rotation pin slidably mating with the rotation-limiting chute.

As such, the cavity of the injection pushrod 14 can act as a motor room in which the motor 16 is installed, the reducer 17 being directly connected with the motor 16, an output shaft of the reducer 17 being connected with the lead screw 18, and the injection pushrod 14 is provided with inner threads therein. The inner threads of the injection pushrod 14 mates with threads of the lead screw 18, and the anti-rotation pin is provided on the exterior of the injection pushrod 14 and slidably mates with the rotation-limiting chute in the outer sleeve 11; a head of the outer sleeve 11 may be provided with a sealing ring sleeved onto the injection pushrod 14, thereby achieving the hermetic seal between the outer sleeve 11 and the injection pushrod 14. The injection pushrod 14 can slide in the cavity of the outer sleeve 11 along the rotation-limiting chute.

The outer sleeve 11 is located outside the injection pushrod 14, and the rotation-limiting chute is located inside the outer sleeve 11, and mating with the anti-rotation pin of the injection pushrod 14, so that when the lead screw 18 rotates, the injection pushrod 14 will not rotate with the lead screw 18, but slide along the rotation-limiting chute. At least one resistive sheet 12 is provided on an inner surface of the outer sleeve 11 along a direction parallel to the resistive sheet slot, and the resistive sheet 12 can be fixedly connected with an electrode outside the outer sleeve 11 through an electrode aperture in the outer sleeve 11.

In operation, when the motor 16 positively drives the reducer 17, the output shaft of the reducer 17 enables drive threads on the lead screw 18 to bring the injection pushrod 14 to move forward, so that a medicine in a reservoir is infused periodically and quantitatively into human body through a conventional infusion device. When the motor 16 reversely drives the reducer 17, the drive threads bring the injection pushrod 14 to move backward and return to its original position, that is, the motor 16 is reset.

In such a configuration, the drive system according to the embodiment is compact, small, light, and easy to use.

In addition, in a preferred implementation of the embodiment, in order to effectively control a pushing force of the injection pushrod 14, a pressure sensor 21 may be further provided, a specific configuration of which is described as follows.

Fixed legs are provided on the outer periphery of the motor 16 and annular bulges are provided on the inner wall of the outer sleeve 11, with inner sides of the fixed legs abutting against the annular bulges. It should be noted that, the inner sides of the fixed legs as described above refer to sides of the fixed legs which are close to the head of the outer sleeve 11, such that the motor 16 cannot move towards the head of the outer sleeve 11. The drive system also comprises an inner cover 19 abutting against outer sides of the fixed legs and an outer cover 20 covering the inner cover 19 and fixedly connected with the outer sleeve 11, with a pressure sensor 21 provided between a top of the inner cover 19 and a top of the outer cover 20.

The inner cover 19 abuts against outer sides of the fixed legs as described above, meaning that when the outer cover 20 is removed, the inner cover 19 and the motor 16 may displace towards the trailing end of the outer sleeve 11.

As such, when the lead screw 18 drives the injection pushrod 14 to move forward, the lead screw 18 will apply a recoil force to the reducer 17 and the motor 16, and the motor 16 will produce a pressing force to the pressure sensor 21 through the inner cover 19, which in turn enables the pressure sensor 21 to sense a pressure, and thus the pushing force of the injection pushrod 14 can be controlled.

The elastic conductive contact sheet 15 mentioned above in the embodiment can be specifically configured as follows.

The elastic conductive contact sheet 15 may inparticularly comprise a conductive ferrule portion sleeved onto the outer periphery of the injection pushrod 14 and at least two conductive contact pin portions connected to the conductive ferrule portion. At least one of the conductive contact pin portions contacts the resistive sheet 12, and at least one of the conductive contact pin portions contacts the conductive sheet 13.

The elastic conductive contact sheet 15 is so sleeved onto the outer periphery of the injection pushrod 14 that the connection reliability between the elastic conductive contact sheet 15 and the injection pushrod 14 is effectively improved.

In addition, in order to easily provide the resistive sheet slot and the conductive sheet slot in the inner wall of the outer sleeve 11, the outer periphery of the outer sleeve 11 according to the embodiment has a square-shaped cross-section, such that the resistive sheet slot and the conductive sheet slot may be just provided in four sidewalls or two opposite sidewalls of the square.

The seal between the outer sleeve 11 and the injection pushrod 14 may be achieved by providing a sealing ring between the head of the outer sleeve 11 and the injection pushrod 14.

In addition, in the drive system according to the embodiment, an encoder for detecting an operation of the motor 16 may be provided on the trailing end of the motor 16. The operation condition of the motor 16 is detected by the coder, if the motor 16 operates abnormally, maintenance can be timely provided to the motor 16.

The embodiment also provides a syringe pump comprising the drive system as described above. Similarly, the syringe pump according to the embodiment can ensure the accuracy of administration.

A syringe pump and a drive system thereof according to the present invention have been described in detail hereinbefore. While specific examples are used herein to set forth principles and embodiments of the present invention, the description of the embodiments above is only provided to facilitate understanding of the method and concept of the present invention. It should be noted that, improvements and modifications can be made by one of ordinary skill in the art, without departing from the principles of the present invention, and such improvements and modifications are intended to fall within the scope of the present invention.

The invention claimed is:

1. A drive system of a syringe pump, comprising:
an outer sleeve having an inner wall provided with a resistive sheet slot and a conductive sheet slots, both of which slot extending axially;
a resistive sheet provided in the resistive sheet slot, and a conductive sheet provided in the conductive sheet slot;
an injection pushrod slidably provided in the outer sleeve, wherein a hermetic seal is maintained between the injection pushrod and the inner wall of the outer sleeve, and a cavity having an opening is provided on the injection pushrod, with the opening of the cavity being provided at a tail end of the injection pushrod;
an elastic conductive contact sheet fixedly provided on the injection pushrod, with one end of the elastic conductive contact sheet being in contact with the conductive sheet and another end being in contact with the resistive sheet; and
a drive device provided in the cavity and driving the injection pushrod to move forth and back.

2. The drive system of claim 1, wherein the drive device comprises a motor provided in the cavity and connected with the outer sleeve, a reducer connected with the motor, and a lead screw connected with the reducer; an inner wall of the cavity is provided with inner threads extending axially and mating with the lead screw; and the inner wall of the outer sleeve is provided with a rotation-limiting chute extending axially, while the injection pushrod is provided with an anti-rotation pin slidably mating with the rotation-limiting chute.

3. The drive system of claim 2, wherein fixed legs are provided on an outer periphery of the motor and annular bulges are provided on the inner wall of the outer sleeve, with inner sides of the fixed legs abutting against the annular bulges; the drive system further comprises an inner cover abutting against outer sides of the fixed legs, and an outer cover covering the inner cover and fixedly connected with the outer sleeve, a pressure sensor being provided between a top of the inner cover and a top of the outer cover.

4. The drive system of claim 1, wherein the elastic conductive contact sheet comprises a conductive ferrule portion sleeved onto an outer periphery of the injection pushrod and at least two conductive contact pin portions connected to the conductive ferrule portion, at least one of the conductive contact pin portions contacting the resistive sheet and at least one of the conductive contact pin portions contacting the conductive sheet.

5. The drive system of claim 1, wherein an outer periphery of the outer sleeve has a square-shaped cross-section.

6. The drive system of claim 1, wherein a sealing ring is provided between a head of the outer sleeve and the injection pushrod.

7. The drive system of claim 2, wherein an encoder for detecting an operation of the motor is provided on a trailing end of the motor.

8. A syringe pump comprising the drive system of any one of claims 1-7.

\* \* \* \* \*